(12) United States Patent  (10) Patent No.: US 9,289,968 B2
Sever et al.  (45) Date of Patent: *Mar. 22, 2016

(54) METHOD FOR HANDLING ADHESIVE LAMINATE SECTIONS

(71) Applicant: 3M INNOVATIVE PROPERTIES COMPANY, St. Paul, MN (US)

(72) Inventors: John M. Sever, Lino Lakes, MN (US); Gordon P. Knutson, Beldenville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/078,768

(22) Filed: Nov. 13, 2013

(65) Prior Publication Data

US 2014/0066866 A1    Mar. 6, 2014

Related U.S. Application Data

(62) Division of application No. 11/916,457, filed as application No. PCT/US2006/022340 on Jun. 8, 2006, now Pat. No. 8,608,889.

(60) Provisional application No. 60/689,212, filed on Jun. 10, 2005.

(51) Int. Cl.
  *B44C 1/17*    (2006.01)
  *B65C 9/18*    (2006.01)
  (Continued)

(52) U.S. Cl.
  CPC ............... *B32B 37/025* (2013.01); *A61K 9/703* (2013.01); *A61K 9/7038* (2013.01);
  (Continued)

(58) Field of Classification Search
  CPC ................ A61F 2013/0276; A61F 2013/0296; A61K 9/7023; A61K 9/703; B26D 7/18; B26D 7/1836; B26F 1/18; B26F 1/20; B26F 1/22; B26F 1/384; B26F 3/002; B29C 2793/00; B29C 2793/0036; B29C 65/48; B32B 37/00; B32B 37/025; B65C 1/025; B65C 2009/0096; B65C 9/0006
  USPC ........... 156/60, 230, 234, 235, 238, 239, 247, 156/249, 250, 256, 257, 264, 265, 267, 268, 156/269, 289, 297, 299, 302, 324, 701, 719
  See application file for complete search history.

(56) References Cited

U.S. PATENT DOCUMENTS 4,475,969 A   10/1984  Reed
4,693,776 A   9/1987   Krampe et al.
(Continued)

FOREIGN PATENT DOCUMENTS

WO    WO 01/22946    4/2001
WO    WO 01/28904    4/2001

*Primary Examiner* — Michael Tolin
*Assistant Examiner* — Brian R Slawski

(57) ABSTRACT

A method of handling an adhesive laminate, wherein the adhesive laminate is provided releasably adhered to a first web, comprising a plurality of cut or punched sections and wherein adjacent sections of the adhesive laminate remain joined to one another in the longitudinal direction of the web through one or more tie points. A first supporting structure and a second supporting structure adjacent to the first supporting structure are provided. The first web is led over the first supporting structure. A second web is provided and led over the second supporting structure, wherein the second web is oriented such that the release surface of the second web faces the first supporting structure. A leading portion of a first section of adhesive laminate from the first web is attached to the release surface of the second web and the second web is advanced such that the first section of the adhesive laminate is detached from a second section of adhesive laminate and the leading edge of the second section of adhesive laminate is adhered to the second web in a spaced apart configuration from the trailing edge of the first section of the adhesive laminate. A transdermal drug delivery device prepared by such a method.

20 Claims, 14 Drawing Sheets

(51) Int. Cl.
  *B29C 65/00*   (2006.01)
  *B32B 37/00*   (2006.01)
  *B32B 38/10*   (2006.01)
  *B32B 38/04*   (2006.01)
  *B65C 9/25*    (2006.01)
  *C09J 5/00*    (2006.01)
  *A61K 9/70*    (2006.01)
  *B29C 65/48*   (2006.01)
  *A61F 13/02*   (2006.01)

(52) U.S. Cl.
  CPC .... *A61F 2013/0296* (2013.01); *B29C 65/4825* (2013.01); *B29C 2793/0036* (2013.01); *Y10T 156/108* (2015.01); *Y10T 156/1064* (2015.01); *Y10T 156/1077* (2015.01); *Y10T 156/1082* (2015.01); *Y10T 156/1084* (2015.01); *Y10T 156/1097* (2015.01)

(56) References Cited

U.S. PATENT DOCUMENTS

| | | |
|---|---|---|
| 4,834,979 A | 5/1989 | Gale |
| 5,223,261 A | 6/1993 | Nelson et al. |
| 5,380,760 A | 1/1995 | Wendel et al. |
| 5,421,946 A | 6/1995 | Flaig |
| 5,492,590 A | 2/1996 | Sakai et al. |
| 5,569,484 A | 10/1996 | Muller et al. |
| 5,656,285 A | 8/1997 | Sablotsky et al. |
| 5,656,286 A | 8/1997 | Miranda et al. |
| 5,681,413 A | 10/1997 | Hille et al. |
| 5,783,269 A | 7/1998 | Heilmann et al. |
| 5,891,290 A | 4/1999 | Deurer et al. |
| 5,935,361 A | 8/1999 | Takahashi et al. |
| 6,004,578 A | 12/1999 | Lee et al. |
| 6,024,976 A | 2/2000 | Miranda et al. |
| 6,059,913 A | 5/2000 | Asmussen et al. |
| 6,149,935 A | 11/2000 | Chiang et al. |
| 6,156,336 A | 12/2000 | Bracht et al. |
| 6,315,854 B1 | 11/2001 | Anhauser et al. |
| 6,334,921 B1 | 1/2002 | Duschek |
| 6,365,178 B1 | 4/2002 | Venkateshwaran et al. |
| 6,461,467 B2 | 10/2002 | Blatchford et al. |
| 6,464,818 B1 | 10/2002 | Schulze et al. |
| 6,527,897 B1 | 3/2003 | Ecker et al. |
| 6,550,517 B1 | 4/2003 | Hilt et al. |
| 6,571,983 B1 * | 6/2003 | Schumann et al. ............ 221/25 |
| 6,592,693 B1 | 7/2003 | Nedblake |
| 6,737,080 B1 | 5/2004 | Schumann et al. |
| 6,977,324 B2 | 12/2005 | Serrano |
| 7,029,549 B1 | 4/2006 | Von Falkenhausen et al. |
| 2002/0119187 A1 | 8/2002 | Cantor et al. |
| 2004/0219195 A1 | 11/2004 | Hart et al. |
| 2004/0238098 A1 | 12/2004 | Bleckmann et al. |

* cited by examiner

METHOD FOR HANDLING ADHESIVE LAMINATE SECTIONS

CROSS-REFERENCE TO RELATED APPLICATIONS

The present application is a divisional of U.S. patent application Ser. No. 11/916,457, filed Dec. 4, 2007 now U.S. Pat. No. 8,608,889, which application is a national stage filing under 35 U.S.C. 371 of PCT/US2006/022340, filed Jun. 8, 2006, which claims priority to U.S. Provisional Application Ser. No. 60/689,212, filed on Jun. 10, 2005, the disclosure of which is incorporated by reference herein in their entirety.

FIELD

The present invention relates to a method for handling adhesive laminate sections. In one embodiment, this invention relates to a method of producing transdermal drug delivery patches.

BACKGROUND

Adhesive laminate sections are often prepared by stamping or cutting the sections from a larger master roll or "jumbo" that is many times longer and may also be wider than an individual section. This process of forming a master roll may be more convenient and efficient than trying to produce many individual sections on a piece-by-piece basis, but the subsequent stamping or cutting process generally results in production of waste material. The amount of waste material and the degree of undesirability of such waste will vary depending on the type of material and the nature of the sections that are created.

As an example, transdermal drug delivery devices often consist of a drug containing adhesive laminate section, a so-called "drug-in-adhesive" patch. The adhesive is placed in contact with a skin surface when in use and the drug passes from the device into the skin. Such devices typically have a release liner that protects the adhesive during storage and which is typically removed just before application of the device to the skin. In some instances it is desirable to use a release liner with a larger surface area than the adhesive portion of the device, as this may make the device easier to handle by a patient and/or may improve the storage stability of the device. Such devices are often referred to as having an extended release liner.

A typical production process for transdermal drug delivery devices in which a master roll is formed and subsequently converted by stamping or cutting individual devices for subsequent packaging and distribution to a patient leaves waste with the same composition as the devices (i.e., containing drug) that must be disposed. Production of devices having an extended liner requires additional converting steps and generates additional waste material.

SUMMARY

It would be desirable to produce adhesive laminate sections from a master roll using a converting process that reduces or eliminates production waste. It would also be desirable to produce transdermal drug delivery devices using a converting process that reduces or eliminates the production of drug-containing waste. It would be further desirable to efficiently produce transdermal drug delivery devices having an extended release liner.

In one embodiment, the present invention is a method of handling an adhesive laminate, wherein the adhesive laminate is provided releasably adhered to a first web, comprising a plurality of cut or punched sections and wherein adjacent sections of the adhesive laminate remain joined to one another in the longitudinal direction of the web through one or more tie points. A first supporting structure and a second supporting structure adjacent to the first supporting structure are provided. The first web is led over the first supporting structure. A second web is provided and led over the second supporting structure, wherein the second web is oriented such that the release surface of the second web faces the first supporting structure. A leading portion of a first section of adhesive laminate from the first web is attached to the release surface of the second web and the second web is advanced such that the first section of the adhesive laminate is detached from a second section of adhesive laminate and the leading edge of the second section of adhesive laminate is adhered to the second web in a spaced apart configuration from the trailing edge of the first section of the adhesive laminate.

In another embodiment, the present invention is a method of handling an adhesive laminate, wherein the adhesive laminate is provided releasably adhered to a first web, comprising a plurality of cut or punched sections wherein adjacent sections of the adhesive laminate remain joined to one another in the longitudinal direction of the web through one or more tie points. A first section of adhesive laminate and a portion of an adjacent second section of adhesive laminate is transferred to a second web, and then the second web is accelerated relative to the first web, thereby detaching the first section from the second section.

In a preferred embodiment the adhesive laminate comprises a drug. The above summary of the present invention is not intended to describe each disclosed embodiment or every implementation of the present invention. The figures and the detailed description that follow more particularly exemplify illustrative embodiments, but should not be construed to unduly limit this invention.

BRIEF DESCRIPTION OF THE DRAWINGS

Preferred embodiments of the invention will now be described in greater detail below with reference to the attached drawings, wherein.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers have been used throughout the figures to denote like parts.

DETAILED DESCRIPTION

Figure 1:
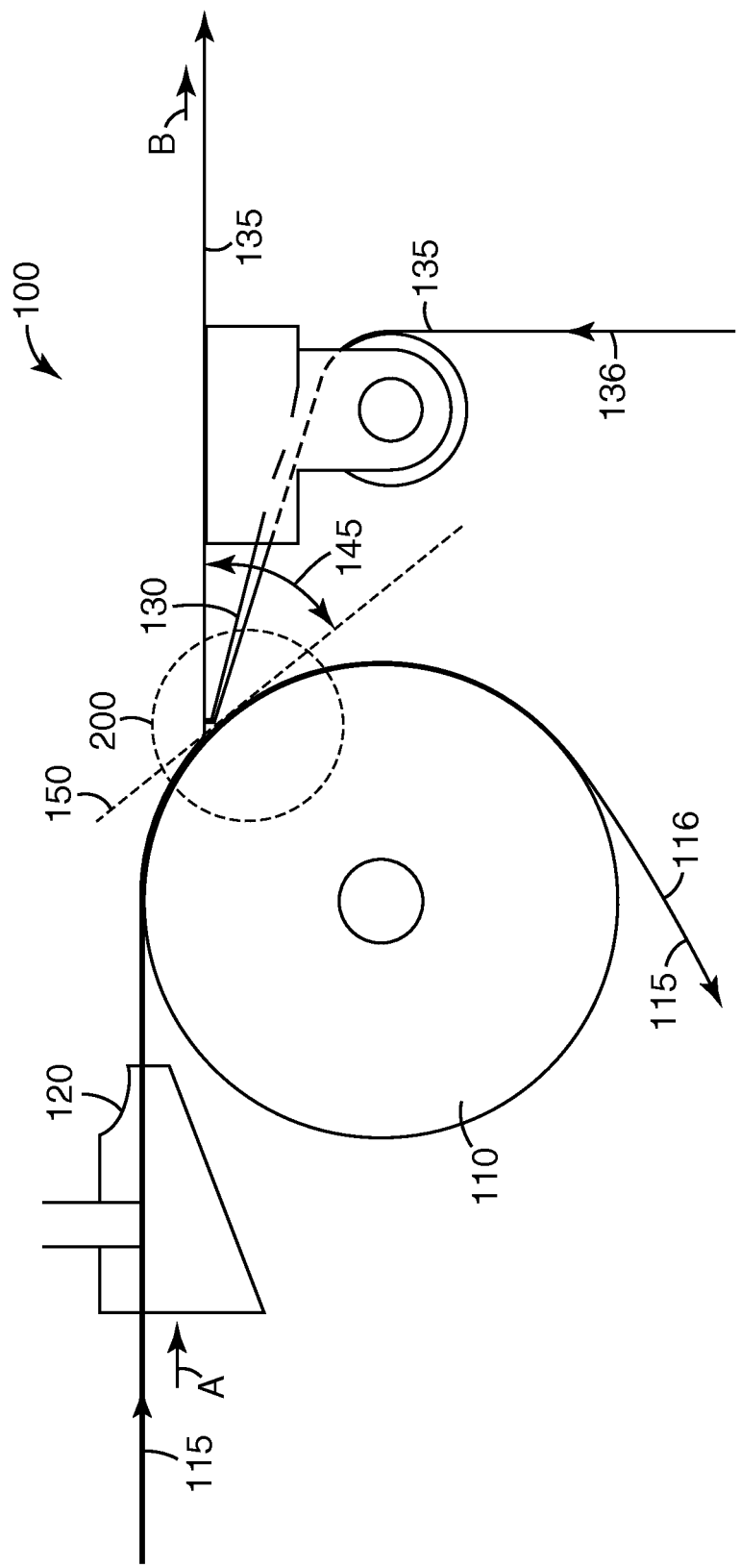
FIG. 1 is a schematic cross-sectional view of a web-handling apparatus.

In the embodiment shown in FIG. 1, the general layout of an apparatus 100 suitable for use in the present invention is illustrated. A first web 115 is supported on a support roll 110. The first web 115 is characterized by a first web release surface 116 that is oriented so that it does not come into direct contact with the support roll 110. The arrow labeled A shows the motion of the first web as it is advanced over the support roll 110. A ribbon guide 120 may be optionally included to help guide the first web 115 as it is advanced towards the support roll 110. In one embodiment, the ribbon guide 120 is used to spread one or more ribbons or strands of web in the transverse or cross direction of the web (i.e., perpendicular to the longitudinal direction of the web or "machine" direction, A) so that each ribbon may be further handled independently. A second web 135 is supported by a nose bar 130. The second web 135 is characterized by a second web release surface 136 that is oriented such that the release surface of the second web 136 faces the support roll 110 where the second web 135 is wrapped around the nose bar 130. The arrow labeled B shows the motion of the second web as it is advanced over the nose bar 130. As will be shown in further detail in FIGS. 4 to 7, the first web is an input material having a partially converted adhesive laminate sheet releasably adhered to it. Sections or patches of the adhesive laminate sheet are transferred to the second web 135 in the vicinity of the nose bar 130 and the first web is removed and may be discarded or re-used. The sections or patches transferred to the second web 135 are placed in a spaced apart fashion, otherwise referred to here as an "island placement" converting process. The second web 135 will typically serve as a final product liner and typically undergoes further converting to prepare individual patch shaped articles having a protective release liner. Although not shown, it should be readily understood that conventional web handling means, such as wind-up rolls, tension bars, and the like, will generally be used to handle both webs before and after they are passed over the support roll 110 or nose bar 130.

The adhesive laminate is generally characterized as a two or more layer structure having an adhesive layer and a backing layer. The adhesive layer may be continuous or discontinuous, but is preferably continuous. The backing is generally continuous, although it may be perforated or otherwise have gaps. In one embodiment, the adhesive and backing layers are continuous.

The adhesive layer will generally be selected according to the desired end use of the articles prepared by the present method. Examples of suitable adhesives include acrylates, silicones, polyisobutylenes, synthetic rubber, natural rubber, and copolymers and mixtures thereof. Further description of suitable adhesives may be found in U.S. Pat. No. 5,656,286 (Miranda et al.), U.S. Pat. No. 4,693,776 (Krampe et al.), U.S. Pat. No. 5,223,261 (Nelson et al.), and U.S. Pat. No. 5,380,760 (Wendel et al.) the disclosures of which are incorporated herein by reference.

Typical examples of flexible films employed as conventional tape backings which may be useful as a backing film include those made from polymer films such as polypropylene; polyethylene, particularly low density polyethylene, linear low density polyethylene, metallocene polyethylenes, and high density polyethylene; polyvinyl chloride; polyester (e.g., polyethylene terephthalate); polyvinylidene chloride; ethylene-vinyl acetate (EVA) copolymer; polyurethane; cellulose acetate; and ethyl cellulose. Coextruded multilayer polymeric films are also suitable, such as those described in U.S. Pat. No. 5,783,269 (Heilmann et al.), the disclosure of which is incorporated herein by reference. Backings that are layered such as polyethylene terephthalate-aluminum-polyethylene composites and polyethylene terephthalate-EVA composites are also suitable. Foam tape backings, such as closed cell polyolefin films used in 3M™ 1777 Foam Tape and 3M™ 1779 Foam Tape are also suitable. Polyethylenes, polyethylene blends, and polypropylenes are preferred polymer films. Polyethylenes and polyethylene blends are most preferred polymer films. In one embodiment, the backing film is translucent or transparent. Additives may also be added to the backing film, such as tackifiers, plasticizers, colorants, and anti-oxidants. It may be desirable to use a flexible backing film, particularly for medical or pharmaceutical applications where the end use product is adhered to skin. In one embodiment, the present method finds particular utility for island placement converting of adhesive laminates having very flexible backings, such as thin polyethylene backings, which are generally difficult to handle in small, individual patch shaped sections.

In one embodiment, the backing film thickness is more than 10 µm, often more than 20 µm, and sometimes more than 40 µm. In another embodiment, the backing film thickness is less than 2 mm, often less than 1 mm, and sometimes less than 150 µm.

The first and second webs 115, 135 may be any conventional film having a release surface. The term release surface is used here in a broad sense as a surface from which an adhesive layer may be removed without undue deformation of the adhesive laminate. The web is intended to serve as a carrier for the adhesive laminate and will generally be a film having sufficient strength to allow handling in ordinary manufacturing processes (e.g., winding, coating, drying, etc.). Suitable webs having a release surface include conventional release liners comprising a known sheet material such as polyester, polyethylene, polypropylene, or polyethylene-coated paper. A suitable release surface may be readily determined by one skilled in the art taking into consideration the nature of the adhesive and the web material. The release surface may have a low surface energy coating (e.g., a fluoropolymer and/or silicone based coating) or it may inherently have a low surface energy. The release surface may be generally smooth or it may have surface texture, for example, to reduce the area of contact between the adhesive and the web. The web may be continuous or perforated, but is preferably continuous. The support roll 110 may be any suitable web-handling roll, including driven and idler rolls. It may be desirable to use a roll having a relatively large diameter so as to minimize the possibility of inadvertently transferring waste portions of adhesive laminate to the second web. Use of a support roll 110 as the first supporting structure is shown in FIG. 1, but any other suitable first supporting structure may be used to support the first web 115, such as a fixed bar or combination of more than one roller and/or bar which serves to adequately support the first web. Likewise, a support roll 160 may be used as the second supporting structure for handling the second web.

Figure 2:
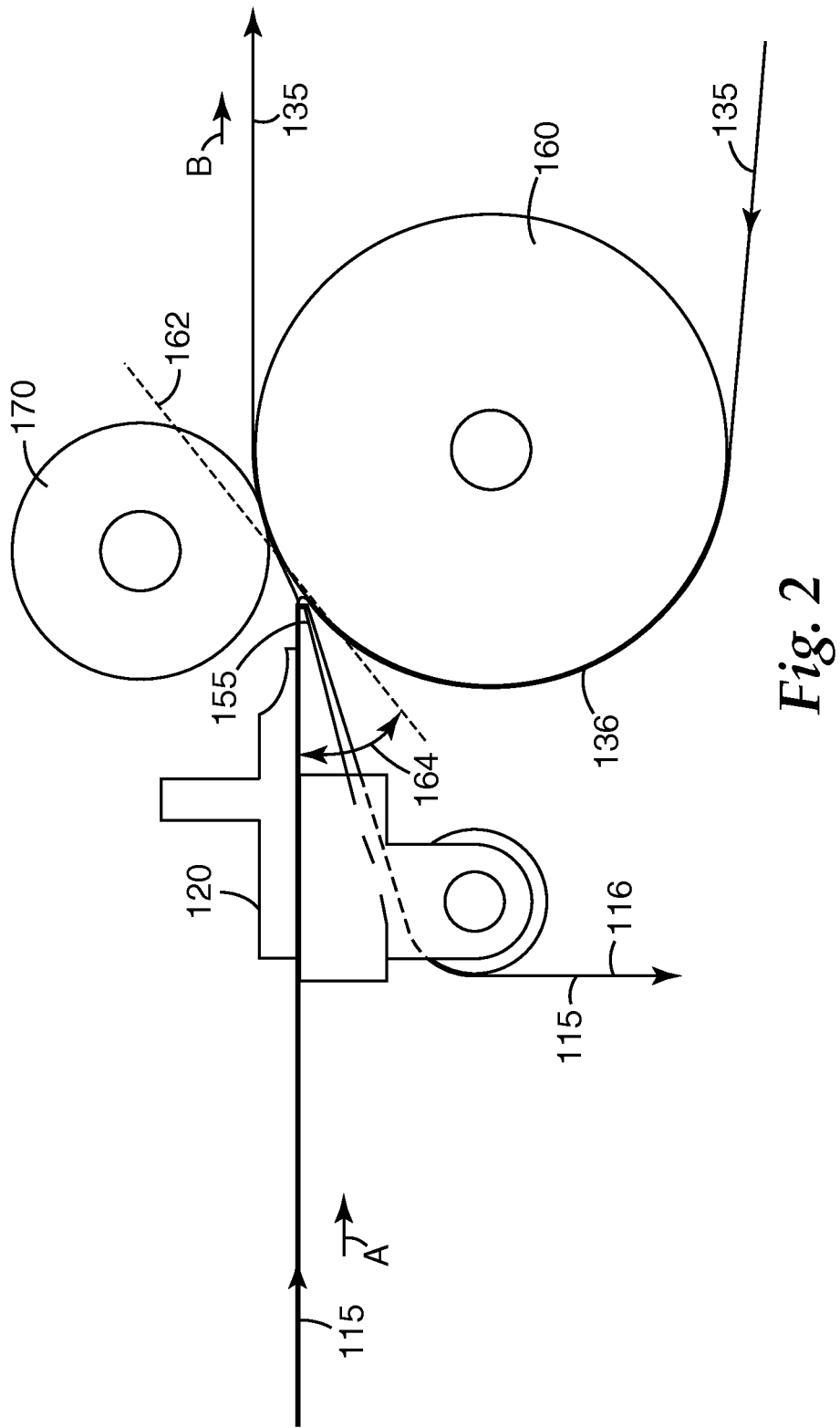
FIG. 2 is a schematic cross-sectional view of a web-handling apparatus.
Figure 3:
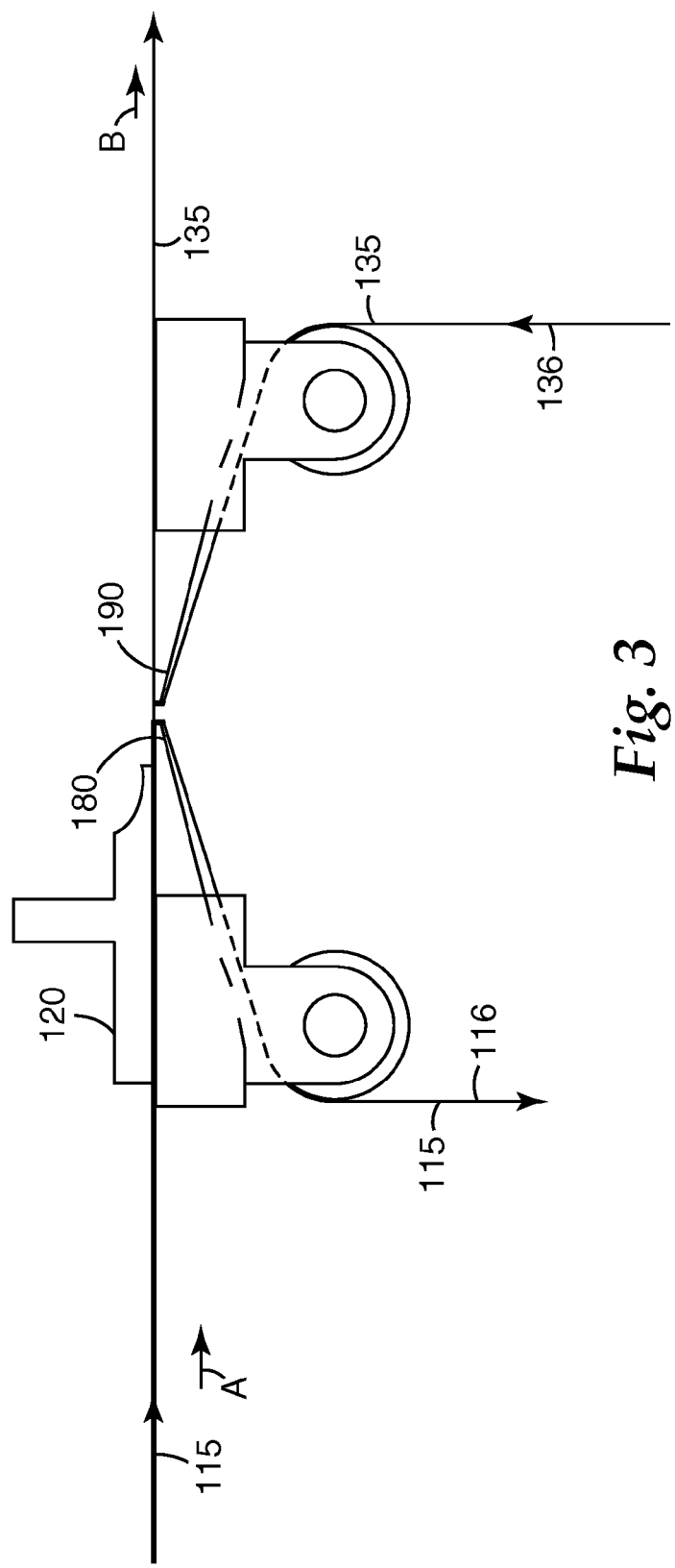
FIG. 3 is a schematic cross-sectional view of a web-handling apparatus.

The nose bar 130 may be any suitable web-handling structure having a shape and configuration that allows the second web to be brought into close proximity to the support roll and also allows the second web to be advanced away from the support roll in such a fashion that sections of adhesive laminate may be transferred from the first web to the second web. The orientation of the nose bar with respect to the support roll may be characterized by a take-off angle 145 shown in FIG. 1. The take-off angle 145 is the angle between the direction of motion of the first web at the point where an adhesive laminate section is transferred (as represented in FIG. 1 by a tangent line 150) and the direction of advancement of the second web 135 as it moves away from the support roll 110. The tangent line 150 is drawn at the point where the adhesive laminate section is removed from the first web. A suitable take-off angle may vary depending on a number of factors including, for example, the types of materials and thicknesses of the adhesive laminate, first web, and second web, and the shapes and sizes of the adhesive laminate sections, the support roll, and the nose bar. The take-off angle is generally between 0 and 120 degrees, often between 10 and 90 degrees, and sometimes between 20 and 60 degrees. Although use of a nose bar is shown in FIG. 1, any other suitable second supporting structure may be used to support the second web 135, such as a roller or combination of more than one roller and/or bar which serves to adequately support the second web and allows for a desired positioning of the second web with respect to the first web. Alternative embodiments are shown in FIGS. 2 and 3. In FIG. 2 a nose bar 155 is used to support the first web 115 and a support roller 160 is used to support the second web 135. An ironing roll 170 may be optionally used to aid in affixing the transferred adhesive laminate sections to the second web. A tangent line 162 is used to define the direction of motion of advancement of the second web 135 in order to define a take-off angle 164. In FIG. 3 a nose bar 180 is used to support the first web and a nose bar 190 is used to support the second web. As shown, the take-off angle in this embodiment is 0 degrees.

Figure 4A:
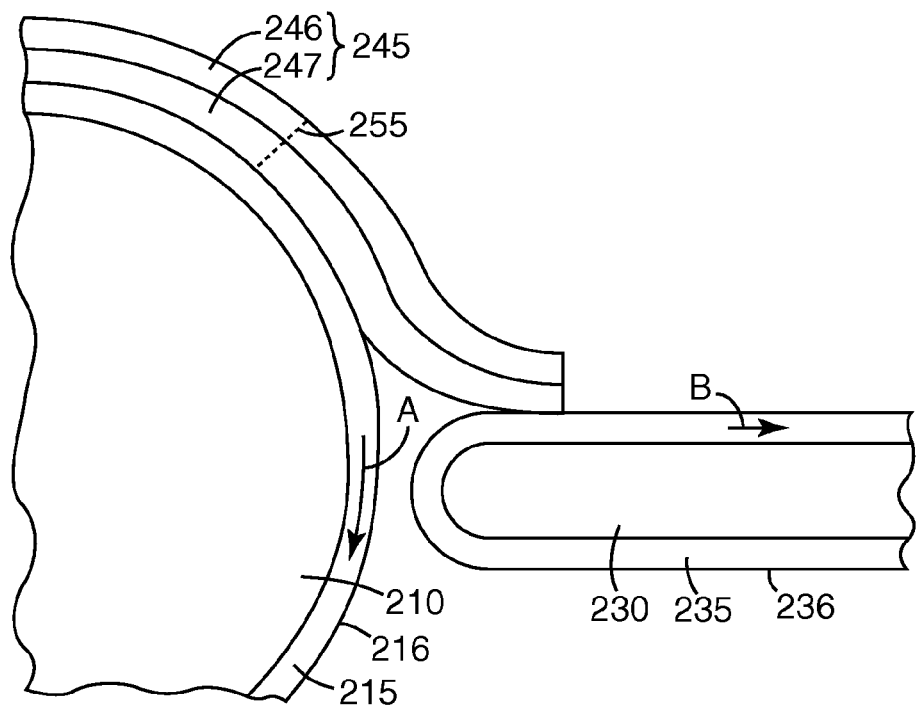
FIG. 4A is a schematic cross-sectional view of a detailed section of FIG. 1 at the area where the adhesive laminate is transferred from the first web to the second web.

FIGS. 4A, B, and C show detailed views of the area labeled 200 in FIG. 1 and illustrate various stages of the method of the present invention. As shown in FIG. 4A, the first web 215 advances along the support roll 210 in the direction of the arrow labeled A. An adhesive laminate 245 comprising a backing 246 and an adhesive 247 is initially adhered to the first web 215 before the first web 215 is advanced along the support roll 210. The leading edge of the adhesive laminate 245 is shown detached from the first web 215 and attached to the release surface 236 of the second web 235, which is supported by the nose bar 230. The adhesive laminate 245 has been cut or punched into sections having the shape of an adhesive patch and the adjacent sections of the adhesive laminate remain joined to one another in the longitudinal direction of the web through one or more tie points 255.

The sections into which the adhesive laminate adhered to the first web is cut or punched are generally in the shape of an adhesive patch, and may be, for example, round, oval, square, rectangular, rectangular with rounded edges, or any other desired shape. In one embodiment, the sections may have gaps or holes, so as to form, for example, a ring shaped patch or to form a patch having a plurality of small through-holes, such as described in United States Patent Application Publication No. 2004-0219195 (Hart et al.), the disclosure of which is herein incorporated by reference. These sections may be prepared, for instance, by making a controlled depth punch through the adhesive laminate such that the adhesive laminate is cut through its full thickness, but such that the web is not cut through its full thickness. Thus, the cut adhesive laminate shape is maintained in place on the web. The terms cutting and punching are intended to include any suitable process that can produce such a sectioned adhesive laminate on a web. Examples of suitable methods include die cutting, such as with rotary or steel-rule dies, stamping, punching, and cutting along a pattern or contour with a knife, blade, laser, or water-jet.

The tie points represent small areas between adjacent patch shaped sections of the adhesive laminate where the sections remain connected. These may be produced, for example, by providing one or more notches in a cutting die, such that one or more points along the edge of the patch shaped section is not cut completely through the thickness of the adhesive laminate. In one embodiment, the tie points may be present as a perforated area along the edge connecting adjacent patches. The connected material remaining at the tie point may be backing and/or adhesive. In one embodiment, the connected material of the one or more tie points is backing and adhesive, that is, a small section of the full thickness of the adhesive laminate that has not been cut or punched. It is generally desirable that the tie points are relatively small. The tie points will have a thickness in the transverse direction of the web that is typically less than 2.0 mm, often less than 1.0 mm, and sometimes less than 0.5 mm in thickness. In one embodiment, the tie points are symmetrically aligned in the transverse direction along the edge of the adjacent patch shaped sections. For example, a single tie point used to connect adjacent patch shaped sections will generally be positioned at the center of the adjacent patch edges. Two tie points used to connect adjacent patch shaped sections will generally be positioned at equal distances on either side of the center of the adjacent patch edges. Three tie points used to connect adjacent patch shaped sections will generally be positioned with one tie point at the center and the other two positioned at equal distances on either side of the center point, and so forth.

The gap or spacing between the support roll and the nose bar is defined as the closest distance between the support roll and the nose bar. This spacing may vary, but it is generally selected so as to avoid having a long portion of unsupported adhesive laminate. In one embodiment, the spacing is selected relative to the lengthwise dimension of a patch shaped section, and may be less than 0.5 times, often less than 0.2 times, and sometimes less than 0.1 times the lengthwise dimension of a patch shaped section. In one embodiment, the spacing may be more than 0.01 times, and sometimes more than 0.05 times the lengthwise dimension of a patch shaped section.

Figure 4B:
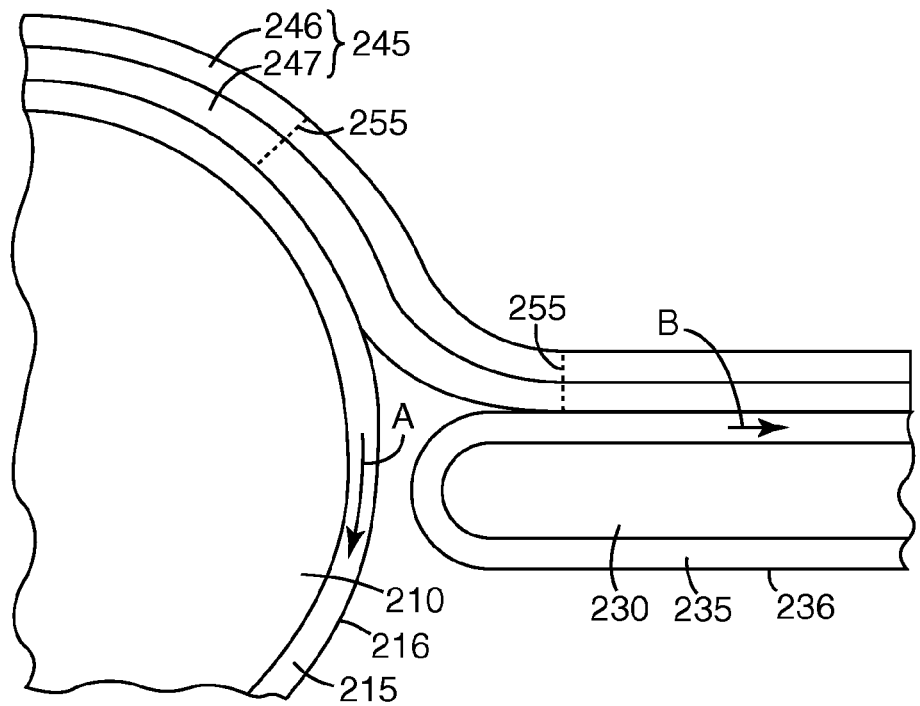
FIG. 4B is a schematic cross-sectional view as in FIG. 4A where the adhesive laminate is further advanced than in FIG. 4A.
Figure 4C:
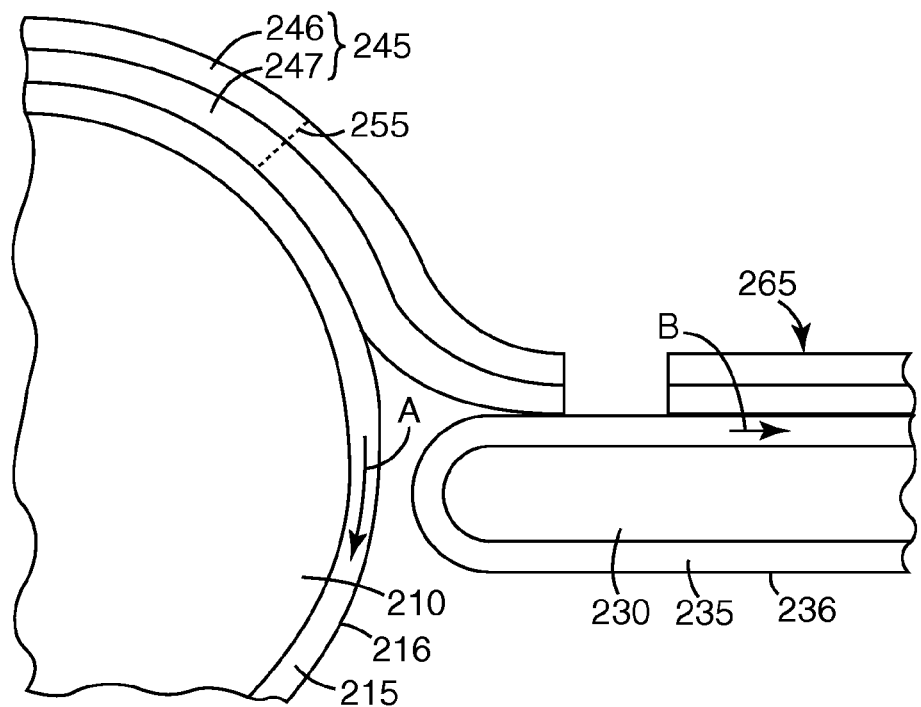
FIG. 4C is a schematic cross-sectional view as in FIGS. 4A-B where a section of adhesive laminate has been detached from the adhesive laminate and is further advanced on the second web.

FIG. 4B shows the adhesive laminate 245 having advanced along the second web 235 in the direction of the motion of the second web 235 (indicated by the arrow labeled B). This advancement is obtained by moving both the first web 215 and the second web 235 appropriate distances in the direction of the arrows labeled A and B, respectively. In one embodiment, the first web 215 and the second web 235 are moved at substantially the same speed during this part of the process. FIG. 4C shows a patch shaped section 265 that has been detached from the adhesive laminate 245 and advanced along the second web 235. This detachment and advancement may be obtained, for example, by momentarily stopping the motion of the first web 215 while continuing the motion of the second web 235. Since the patch shaped section 265 is adhered to the second web 235, it is thus pulled and detached from the rest of the adhesive laminate 245. It is not necessary, however, to stop the motion of the first web 215, as the same result may be obtained by providing a differential rate of motion between the first 215 and second webs 235. In particular, if the first web 215 advances more slowly than the second web 235, then the patch shaped section 265 will be pulled away from the remainder of the adhesive laminate 245 and thereby exert a force that will cause the tie point(s) 255 to be severed. In one embodiment, the second web is advanced over the nose bar in a continuous motion (that is, without stopping) and more preferably at a substantially constant rate. In one embodiment, the first web is advanced at a constant rate and the second web is intermittently accelerated and decelerated in order to detach the patch shaped sections. The second web may be accelerated in a generally step-wise fashion, that is, it is rapidly accelerated to a faster speed than the first web to quickly cause detachment. After detachment, the second web may be held at the faster speed for a given time period to obtain the desired spacing of patch shaped sections on the second web. For example, the second web may be held at a uniform faster speed for a given time period and then decelerated in a step-wise fashion to substantially the same rate as the first web. In an alternative embodiment, the second web may be gradually slowed to match the rate of the first web in such a fashion as to provide the desired spacing of patch shaped sections on the second web.

Alternatively, the second web may be held at a constant rate and the first web is intermittently accelerated and decelerated in order to detach the patch shaped sections.

In more general terms, the detachment is facilitated by accelerating the second web relative to the first web. It should be understood that this relative acceleration may be accomplished by many different combinations of speeds of the first and second webs, including those combinations described above, but also included any other combinations of speeds. For example, both webs may move in a predetermined pattern of constantly changing speeds while still providing the desired relative motion between the two webs. In one embodiment the two webs are moved at substantially the same speed during the time that a patch shaped section is being transferred from the first web to the second web. The term substantially the same speed should be understood to encompass small fluctuations or differences in speed between the two webs as long as these small fluctuations or differences will not lead to any change in the process relative to the process where the speed of the two webs is identical. For example, this matching of speed is intended to minimize any stretching or tensile forces that might lead to irreversible deformation of the patch shaped section while it is contact with both webs. Although not wishing to be bound by theory, it is believed that the patch shaped section spanning the gap is held in place by the adhesion of the portion of the section in contact with the first web during the time that the patch shaped section on the second web is detached (i.e., the leading edge of the section slips over the second web while the patch shaped section ahead of it is detached). An optional ironing roll 170, such as shown in FIG. 2, may be positioned such that it contacts the leading patch shaped section before it is detached. This may increase the adhesive force between the patch shaped section and the second web prior to detachment and thereby assist in detaching the leading section from the remainder of the adhesive laminate.

Figure 5:
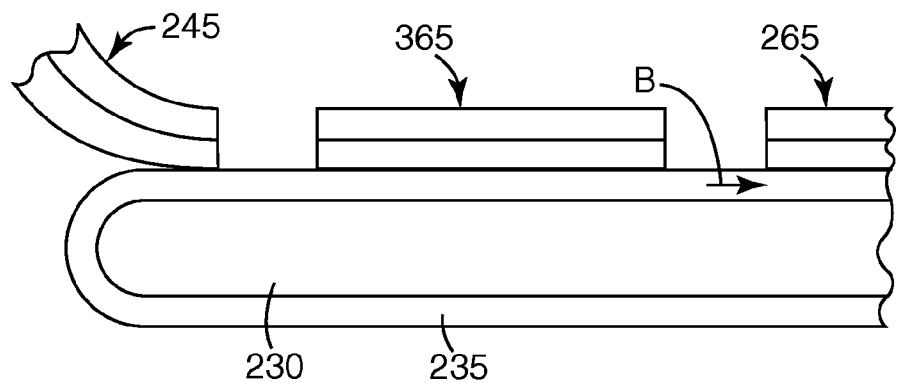
FIG. 5 is a schematic cross-sectional view as in FIGS. 4A-B where multiple patches have been detached from the adhesive laminate.
Figure 6:
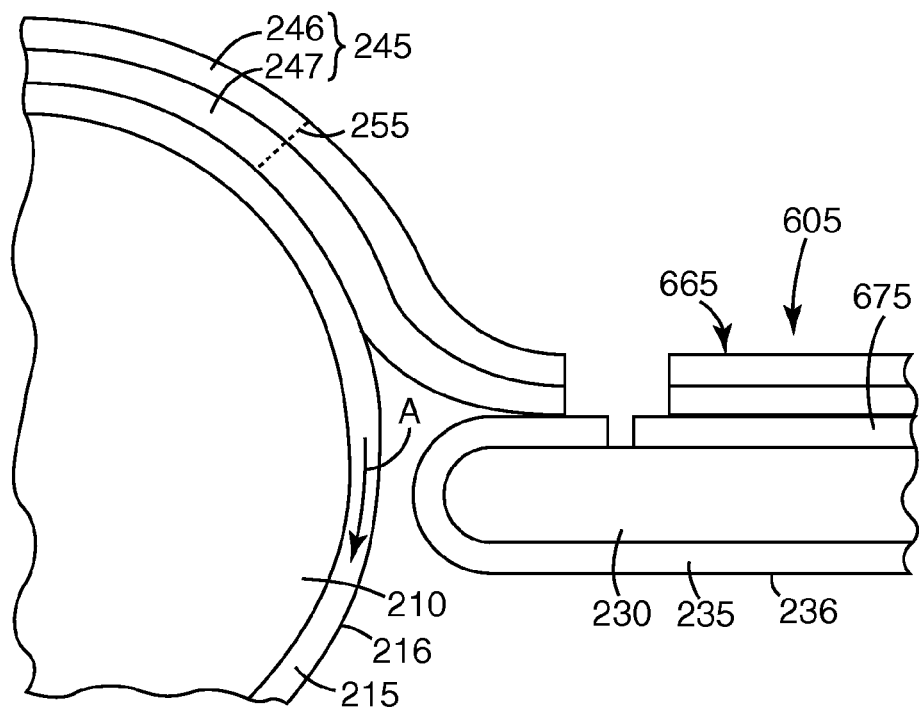
FIG. 6 is a schematic cross-sectional view as in FIGS. 4A-B where a finished device has been separated from the second web.
Figure 7:
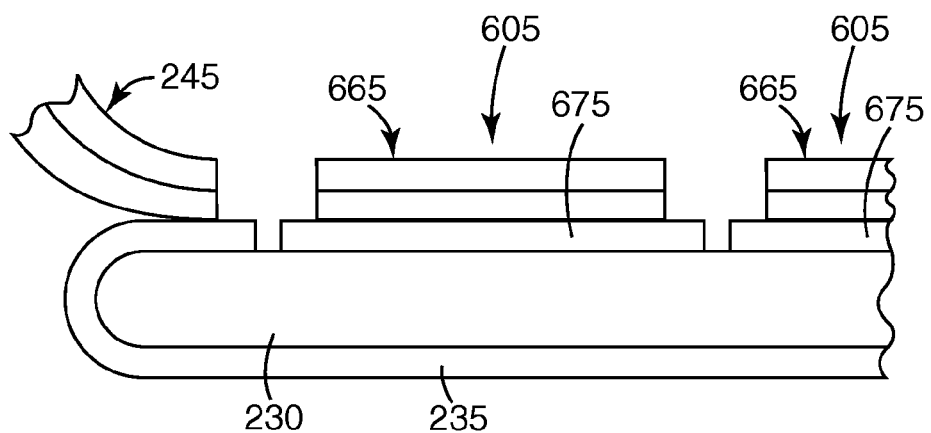
FIG. 7 is a schematic cross-sectional view as in FIG. 6 where multiple finished devices have been separated from the second web.

FIG. 5 shows the result of repeating the process described above so that a second patch or section 365 has been detached from the adhesive laminate 245. By adjusting the relative rates of motion of the two webs, the spacing of the patch shaped sections 365, 265 on the second web can be adjusted to any desired distance. The distance between the spaced sections may be held constant or varied in any desired arrangement by proper adjustment of the web speeds. This process may be repeated any multiple of times. The resulting web with spaced apart patches may be stored for future use, for example, by winding into a large roll or it may be further converted directly into individual adhesive patches. As shown in FIG. 6, the second web 235 has been cut or punched to separate a drug delivery device 605 made up of an adhesive patch 665 adhered to a release liner 675. As shown, the release liner 675 is larger in area than the adhesive patch, that is, it is an extended liner. FIG. 7 further shows the result of repeating the steps described previously.

Figure 8:
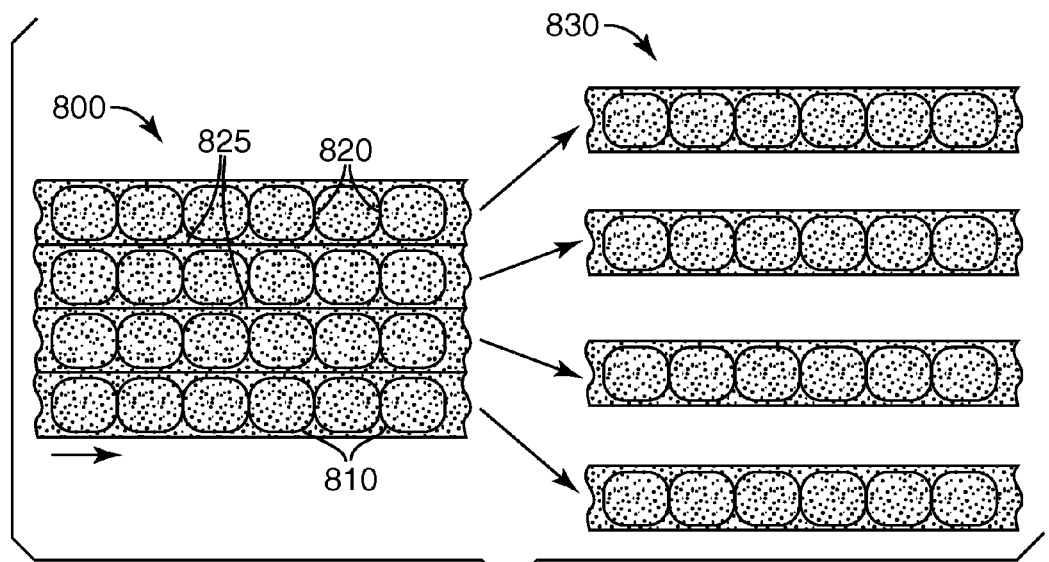
FIG. 8 is a schematic plan view of four ribbons cut from a full-width web having partial cuts in the shape of patches.
Figure 9:
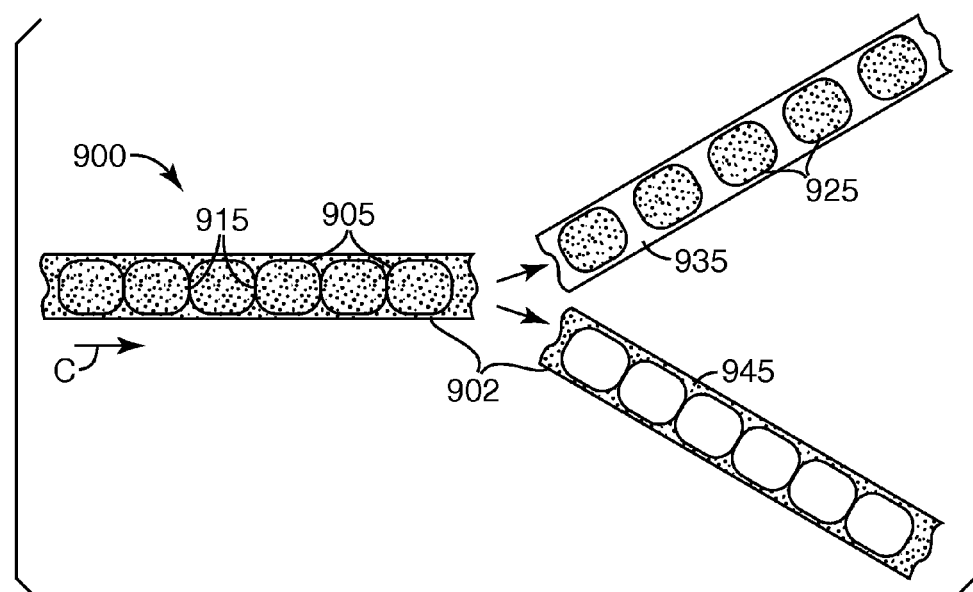
FIG. 9 is a schematic plan view of a single ribbon as in FIG. 8 from which individual patches are separated and spaced apart on a second web.

FIGS. 8 and 9 show the disposition of adhesive laminate in one embodiment starting with a first web having an adhered, continuous layer of adhesive laminate and finishing with individual patches that have been adhered in a spaced apart arrangement on a second web. FIG. 8 shows an input web 800 comprising an adhesive laminate adhered to a first web having a release surface. The adhesive laminate comprises cut or punched patch shaped sections 810 having one or more tie points 820 connecting adjacent sections of the adhesive laminate to one another in the longitudinal direction of the web. As shown, the adhesive laminate and web are cut along the lines 825 into four individual ribbons 830 that may be processed further. The number of individual ribbons may be varied and will typically be between 1 and 10, but this process may be equally applied to any number of individual ribbons.

FIG. 9 shows a single ribbon 900 of material made up of an adhesive laminate adhered to a first web 902. The adhesive laminate has been cut into patch shaped sections 905, shown here as rectangular sections with rounded corners. These patch shaped sections 905 are connected in the longitudinal direction of the web (shown by the arrow C) by one or more tie points 915. This input ribbon 900 is supported by a first supporting structure (not shown here) as previously described. The patch shaped sections 905 are transferred to a second web 935, which is supported by a second supporting structure (not shown here) as previously described. The relative rates of motion of the two webs are adjusted so that the one or more tie points 915 are severed and the transferred patches 925 are arranged in a spaced apart configuration. The remaining adhesive laminate material (or waste material) 945 remains with the first web as it is removed from the support roller and may be recycled or disposed of as appropriate.

Figure 10:
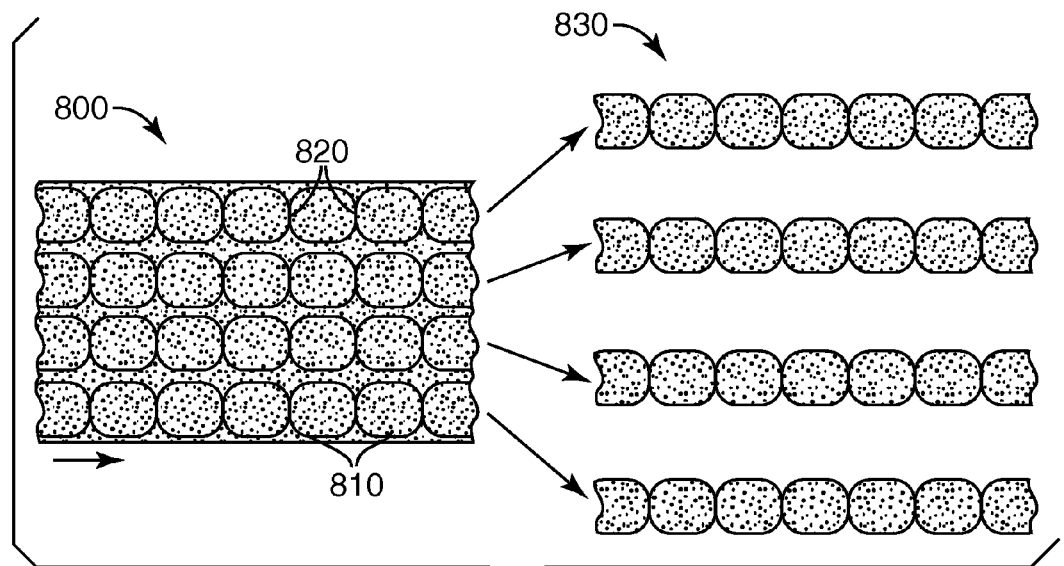
FIG. 10 is a schematic plan view of four ribbons cut from a full-width web having partial cuts in the shape of patches.
Figure 11:
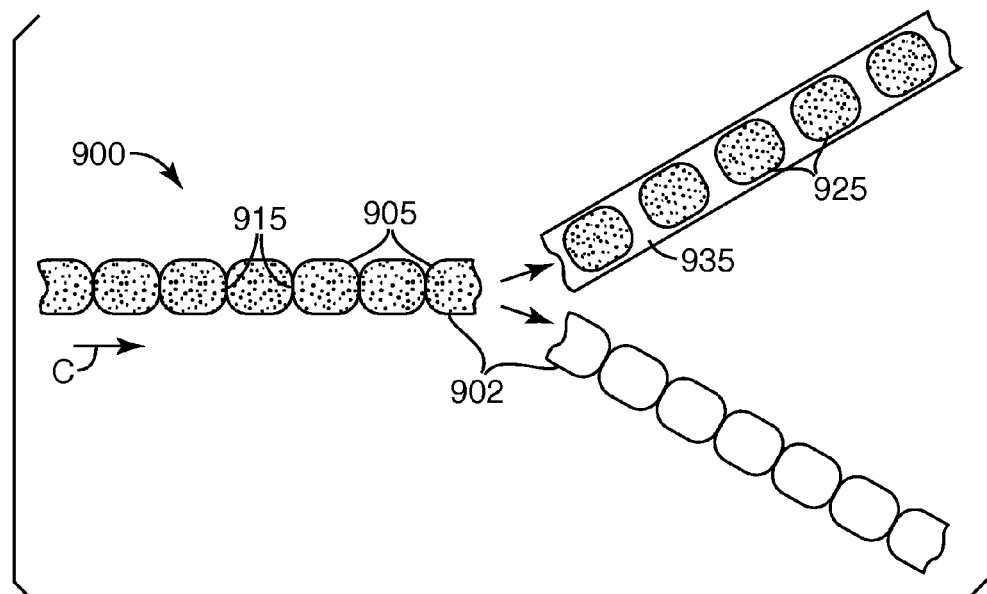
FIG. 11 is a schematic plan view of a single ribbon as in FIG. 10 from which individual patches are separated and spaced apart on a second web.
Figure 12:
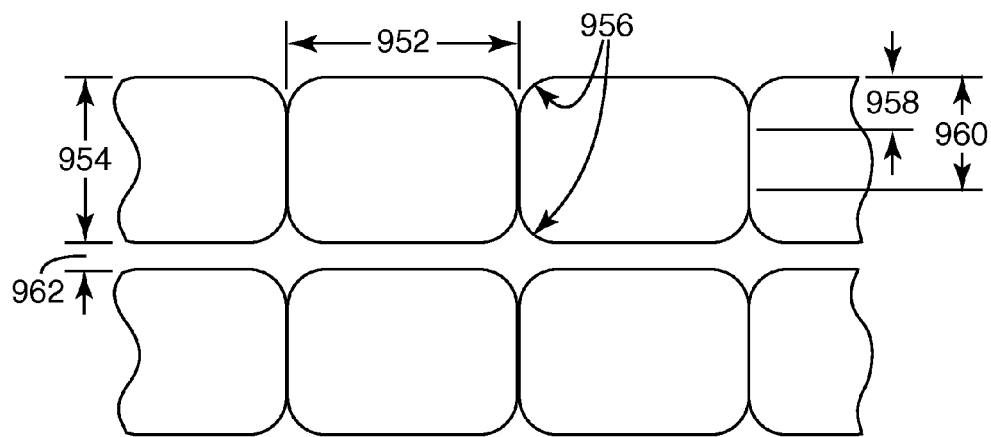
FIG. 12 is a schematic plan view of a detailed section of two ribbons.

An alternative embodiment is shown in FIGS. 10 and 11 where the ribbons 830 are prepared by die cutting through both the adhesive laminate and first web 800 along the outer edges of the patch shaped sections 810. The input web 800 is not cut along the transverse lines connecting adjacent patches, but the adhesive laminate is cut along the transverse lines connecting adjacent patches, with the exception of one or more tie points 820. The strands of adhesive laminate and input web between the ribbons are removed and may be recycled or disposed of as appropriate. An individual ribbon 900 is then further converted by transferring the patch shaped sections 905 to a second web 935 by detaching and spacing the adjacent patches 925 as previously described. The first web 902 is removed and may be recycled or disposed of as appropriate. The size and spacing of rectangular patch shaped sections having rounded corners may be characterized as shown in FIG. 12 by a patch length 952, a patch width 954, a corner radius 956 or other suitable curvature, tie point spacing(s) 958, 960, and lane spacing 962 between adjacent ribbons.

Figure 13:
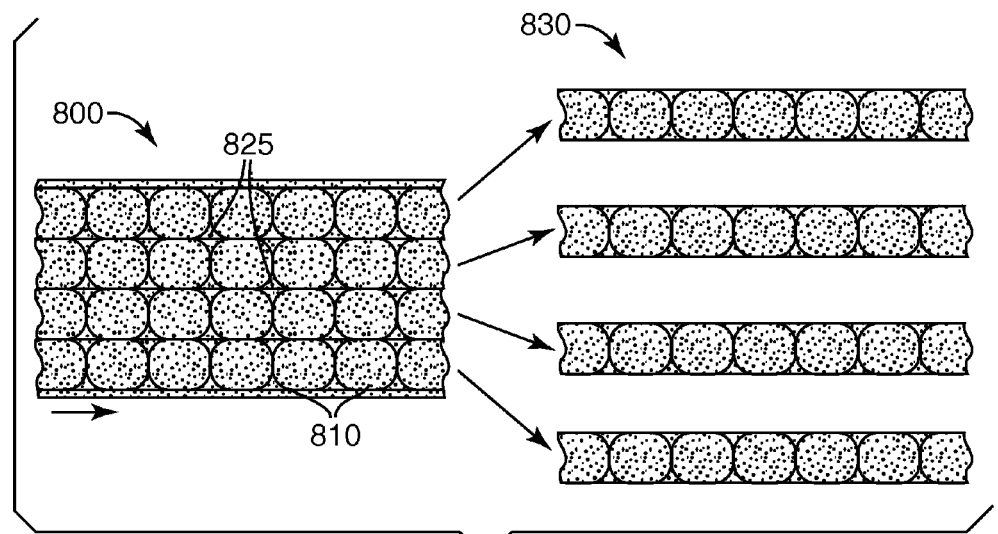
FIG. 13 is a schematic plan view of four ribbons cut from a full-width web having partial cuts in the shape of patches.
Figure 14:
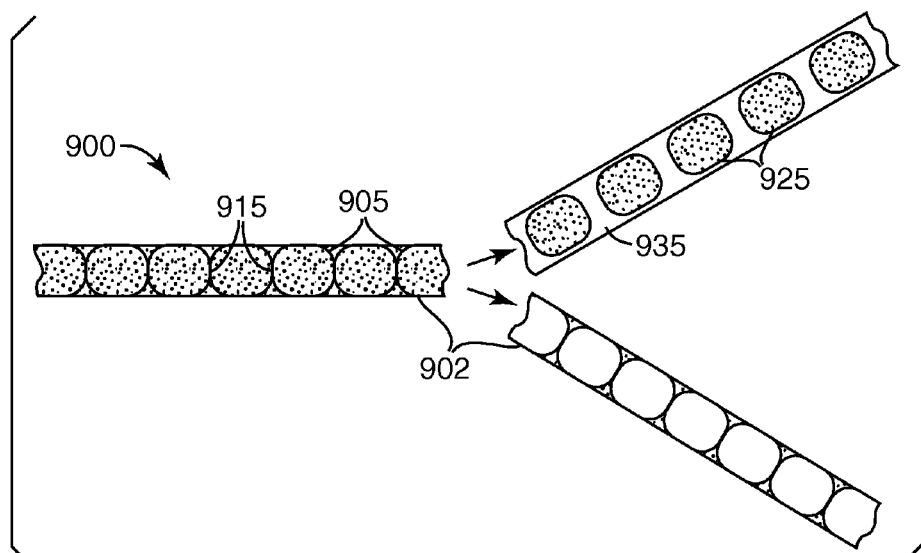
FIG. 14 is a schematic plan view of a single ribbon as in FIG. 13 from which individual patches are separated and spaced apart on a second web.
Figure 15:
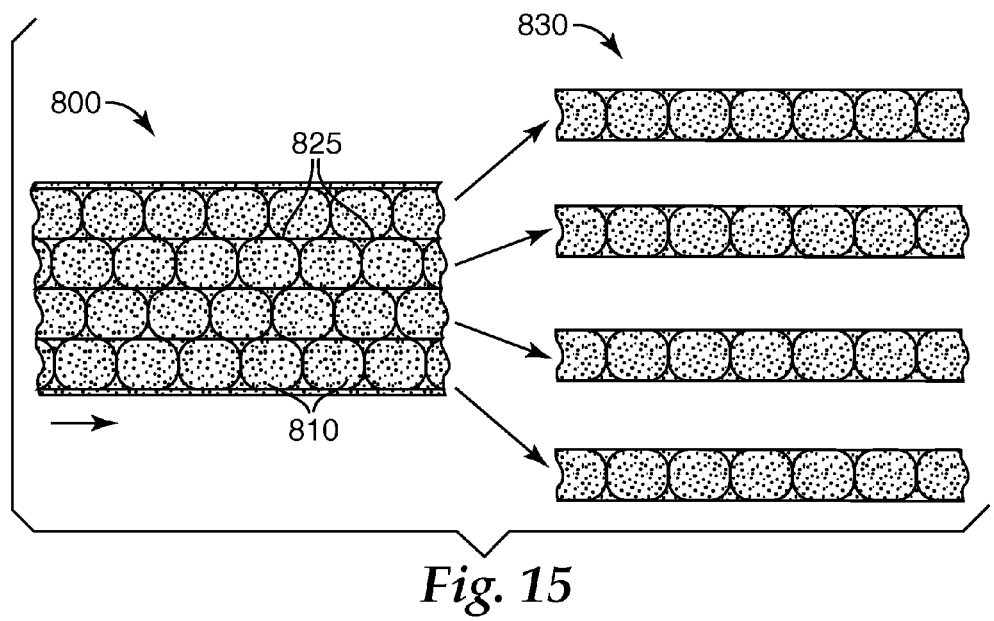
FIG. 15 is a schematic plan view of four ribbons cut from a full-width web having partial cuts in the shape of patches.

Still another embodiment is shown in FIGS. 13 and 14. The input web 800 is processed in a similar fashion to that shown in FIG. 8 with the exception that the patch shaped sections not only abut patch shaped sections in the longitudinal direction of the web, but also abut patch shaped sections in the transverse direction of the web (i.e., abut patch shaped sections in adjacent ribbons). This arrangement reduces the amount of adhesive laminate that does not get converted into patches. Although this might be done by die cutting the patch shaped sections 810 and separately cutting the liner cuts 825 as described in the embodiment of FIG. 8, this is more conveniently achieved by die cutting both the patch shaped sections 810 and the liner cuts 825 with a single die. The patch shaped sections 810 are only die cut through the adhesive laminate and the liner cuts 825 are die cut through both the adhesive laminate and the input web 800. The individual ribbons 830 thus prepared may be further converted in the same way as described in the embodiment shown in FIG. 9, thereby producing patches 925 spaced apart on a second web 935 and a first web 902 having small, unconnected adhesive laminate pieces as shown in FIG. 14. In one embodiment, it is preferred to use a rotary die having a thin silicone foam insert adhered to the milled surface of the rotary die. This foam holds a slight pressure on the backing of the adhesive laminate as it is being cut, but the release property of the silicone foam prevents the triangular shaped waste pieces from building up in the die cavity. Although shown in a side-by-side arrangement in FIG. 13, the patches in adjacent ribbons may be staggered with respect to one another. For example, the alignment of patches may be shifted one-half the length of a patch with respect to each other so that the small triangular piece on one ribbon abuts the flat side of an adjacent patch rather than abutting another small triangular piece, as shown in FIG. 15. Such an arrangement may be advantageous, for example, in allowing for relative ease of die-cutting.

Figure 16:
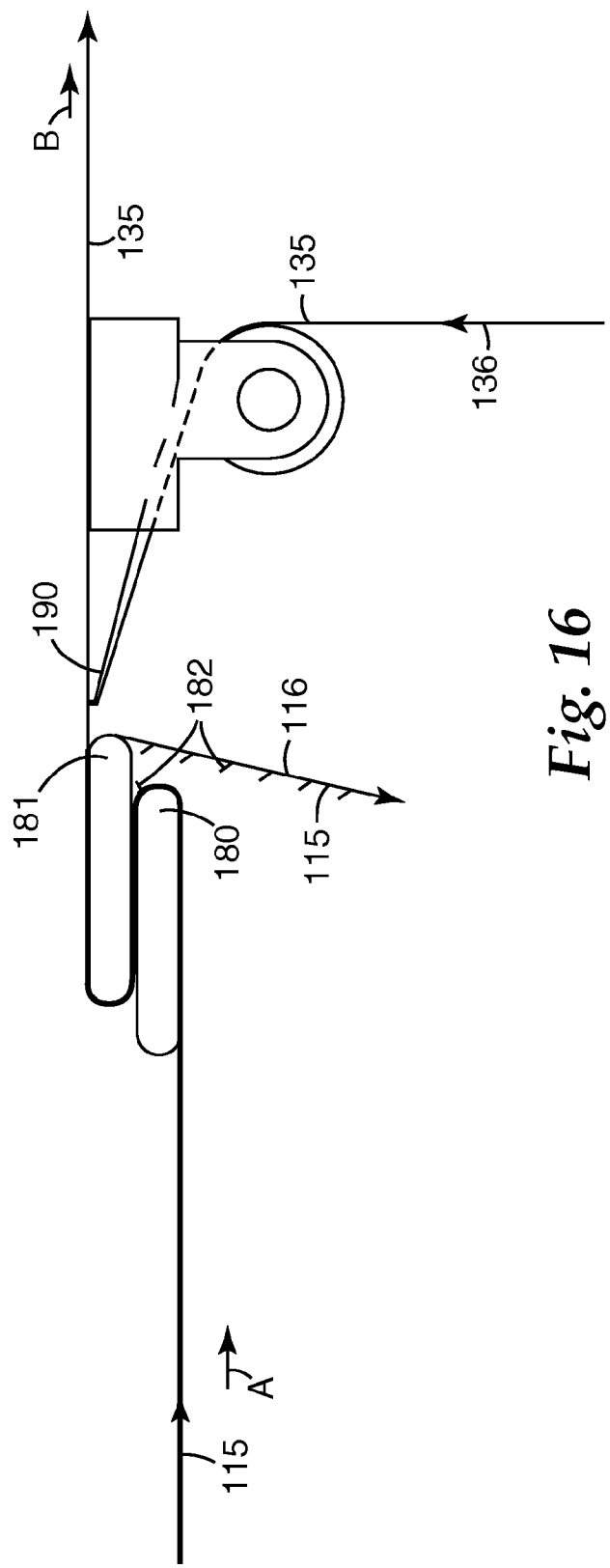
FIG. 16 is a schematic cross-sectional view of a web-handling apparatus.

Still another embodiment is shown in FIGS. 16-20. The apparatus shown in FIG. 16 is similar to that of FIG. 3, with the exception that the first web 115 is supported by a first nose bar 180 and a second nose bar 181. A third nose bar 190 is used to support the second web 135. The first web 115 follows an S-shaped path, first wrapping around the first nose bar 180 and then subsequently wrapping around the second nose bar 181, prior to the point of transfer of an adhesive laminate section to the second web 135. The apparatus may be operated in the same manner as previously described, however it may be advantageous to use this configuration with an adhesive laminate as described in FIGS. 17-19.

Figure 17:
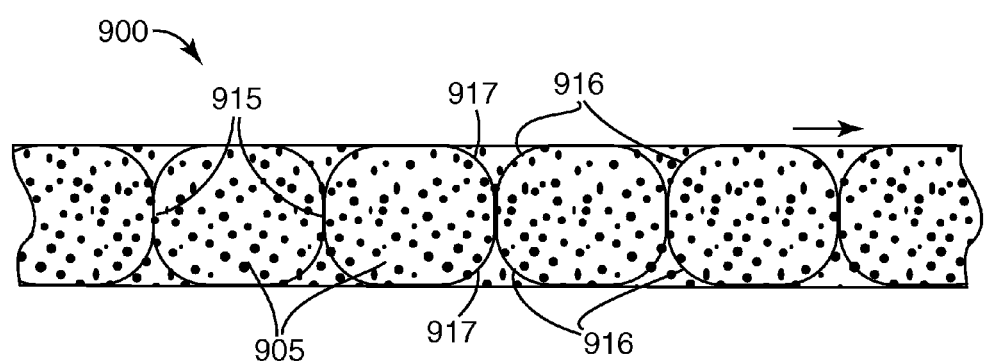
FIG. 17 is a schematic plan view of a single ribbon of patches.

The adhesive laminate of FIG. 17 is similar to that shown in FIG. 14, having an individual ribbon 900 with patch shaped sections 905 connected by one or more tie points 915. The leading, curved edges 917 of the patch shaped sections 905, or a portion of same, are die cut through the adhesive laminate, but not through the release liner, as described in foregoing embodiments. The trailing, curved edges 916 of the patch shaped sections 905 are cut entirely through both adhesive laminate and release liner. The die cut pattern is shown in more detail in FIG. 18. The straight dashed line represents the tie points 915 where the adhesive laminate is partially, but not entirely cut, thus allowing for a weak connection between adjacent patch-shaped sections. The curved dashed lines represent the leading, curved edges 917 of the patch-shaped sections where the adhesive laminate is entirely through cut, but the release liner is not cut. The solid lines represent trailing, curved edges 916 of the patch-shaped sections, as well as the edges of the ribbon, where the adhesive laminate and release liner are cut through entirely.

Figure 18:
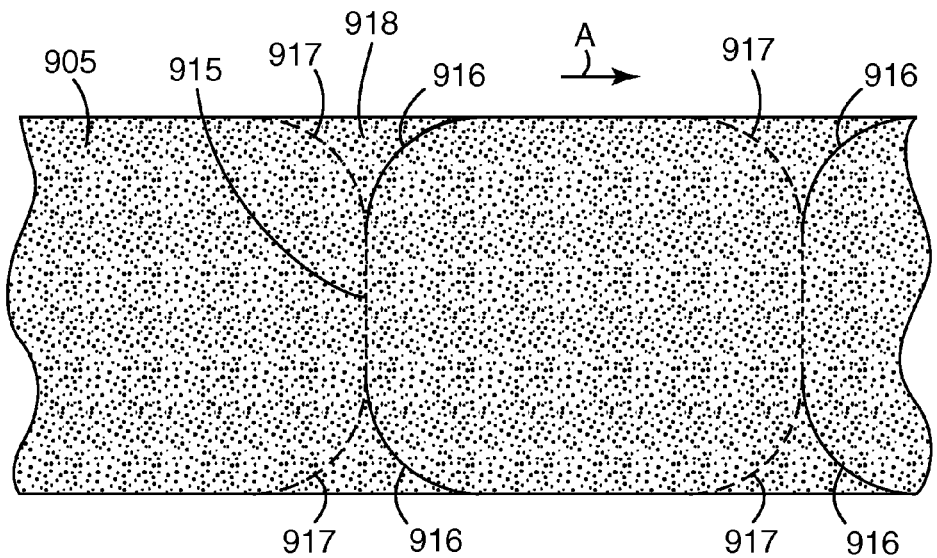
FIG. 18 is schematic plan view of a detailed section of the ribbon of FIG. 16.
Figure 19:
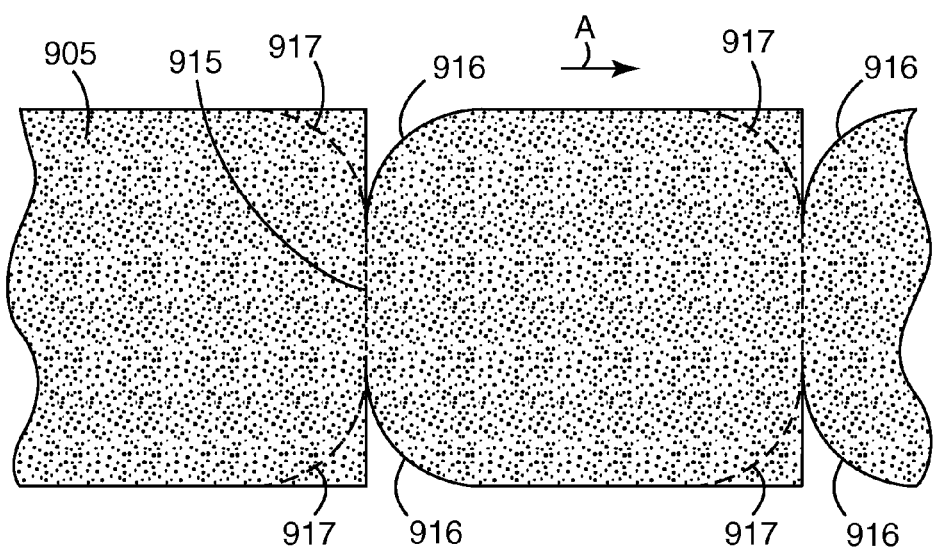
FIG. 19 is schematic plan view of a detailed section of the ribbon of FIG. 16 just prior to a transfer step.
Figure 20:
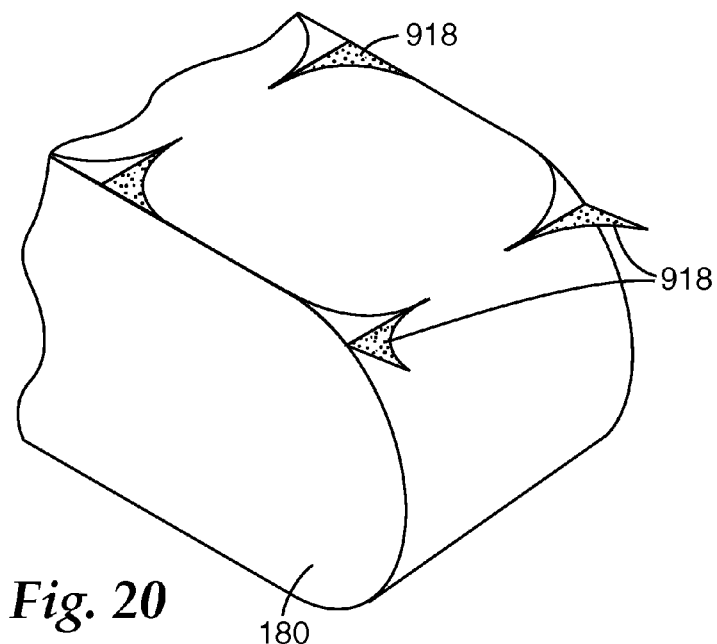
FIG. 20 is a perspective view of a portion of the ribbon of FIGS. 17-19 as the triangular sections are folded away from the web.
Figure 21:
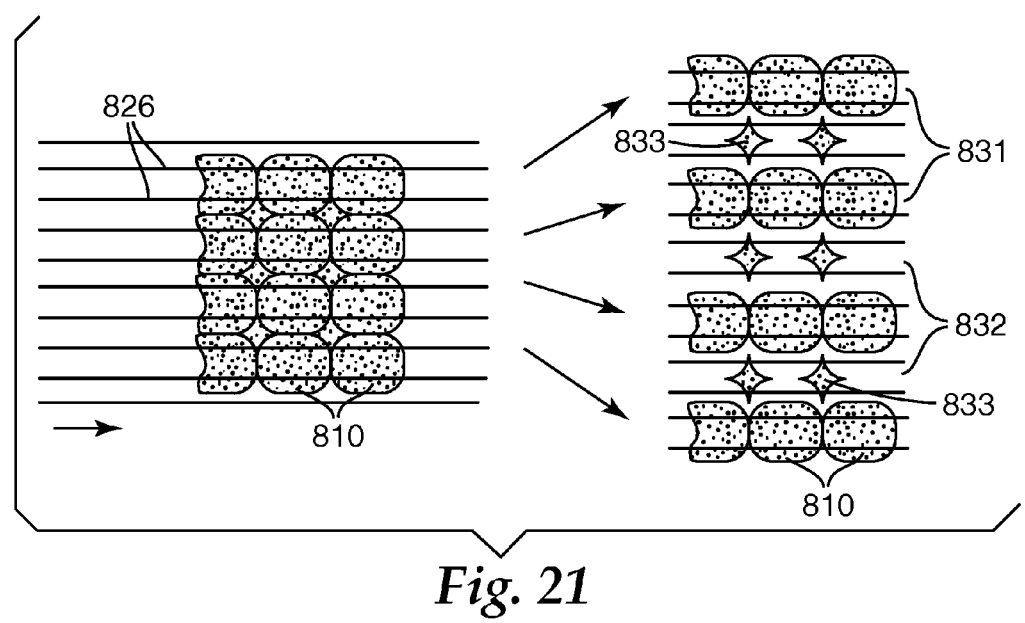
FIG. 21 is a schematic plan view of another embodiment of the present invention.

As the web of FIGS. 17-18 wraps around the first nose bar 180, the small, triangular sections 918 extend away from the nose bar, shown as a small tab 182 in FIG. 16. The small triangular sections 918 are then pressed backwards by the second nose bar 181, so that the web appears as in FIG. 19 as it passes around the second nose bar 181 and to the transfer point. As shown in FIG. 19, the leading portion of the small triangular sections 918 is folded back under the web. This eliminates the possibility that a small triangular section may remain adhered to a patch-shaped section during transfer. This may be particularly preferable when the adhesive is highly aggressive, thus increasing the likelihood that the small, triangular section may re-adhere to the transferred patch-shaped section despite a through cut through the adhesive laminate in that area. Folding of the triangular section back against the nosebar 181 pins it in place and makes it very difficult, if not impossible, for it to accidentally adhere to a transferred patch-shaped section. FIG. 20 shows a perspective view of the webs shown in FIGS. 16-19 to better illustrate how the triangular sections 918 fold away from the main portion of the web as they wrap around the first nose bar 180 and how the second nose bar (not shown) pins them back. Still another embodiment is shown in FIG. 21. The adhesive laminate with patch shaped sections may be prepared in a manner similar to that described in connection with FIG. 13. As shown in FIG. 13, however, the backing and adhesive layers are cut into patch shaped sections 810 and the release liner has liner cuts 825 at the edges of the patch shaped sections 810 so that the web with a width of four patch-shaped sections 810 may be separated into four ribbons (along with two edge or weed strips), whereas in the embodiment of FIG. 21 the release liner has liner cuts 826 spaced so that the full web may ultimately be separated into seven ribbons (along with two edge or weed strips). As the liner cuts 826 in FIG. 20 are not contiguous with the edges of the patch shaped sections 810, it is necessary to make these cuts independently from the cuts made to produce the patch shaped sections 810. For example, a partial die cut of the patch shaped sections into the adhesive laminate may be performed on a first liner, while the liner cuts 826 are made on a second liner. The adhesive laminate can then be transferred to the second liner to produce a configuration as shown in FIG. 21. The ribbons may then be separated to give four product ribbons 831 and three waste ribbons 832, as shown. Each waste ribbon 832 retains the small, waste portions of adhesive laminate 833, which can then be handled conveniently. The product ribbons 831 can be further processed in the same fashion as described in foregoing embodiments to provide individually placed patches on a release liner.

In one embodiment the adhesive laminate patches prepared may comprise a drug. Suitable transdermal drug delivery devices include gelled or liquid reservoirs, such as in U.S. Pat. No. 4,834,979 (Gale), so-called "reservoir" patches; devices containing matrix reservoirs attached to the skin by an adjacent adhesive layer, such as in U.S. Pat. No. 6,004,578 (Lee, et al.), so-called "matrix" patches; and devices containing pressure-sensitive adhesive reservoirs, such as in U.S. Pat. No. 6,365,178 (Venkateshwaran et al.), U.S. Pat. No. 6,024,976 (Miranda et al.), and U.S. Pat. No. 6,149,935 (Chiang et al.), so-called "drug-in-adhesive" patches, the disclosures of which are incorporated herein by reference. The term reservoir is used herein to describe a portion of the patch which houses a drug and as described above may be liquid, solid, adhesive, or any other suitable form.

The length of time that the device remains in a delivering relationship is typically an extended time, for example, from about 12 hours to about 14 days. In certain embodiments, the length of time that the reservoir remains in a delivering relationship is about 1 day (i.e., daily dosing), about 3 to 4 days (bi-weekly dosing), or about 7 days (weekly dosing).

In one embodiment, the reservoir may contain other additives or excipients in addition to the pharmaceutically active agent. Such additives include pharmaceutically acceptable materials that may be used as skin penetration enhancers (i.e., substances that increase the permeation rate of a drug across or into the skin) or solubilizers (i.e., substances that effectively solubilize a drug) in transdermal drug delivery systems. Suitable materials used as skin permeation enhancers include $C_8$-$C_{20}$ fatty acids such as isostearic acid, octanoic acid, and oleic acid; $C_8$-$C_{20}$ fatty alcohols such as oleyl alcohol and lauryl alcohol; lower alkyl esters of $C_8$-$C_{20}$ fatty acids such as ethyl oleate, isopropyl myristate, butyl stearate, and methyl laurate; di(lower) alkyl esters of $C_6$-$C_8$ diacids such as diisopropyl adipate; monoglycerides of $C_8$-$C_{20}$ fatty acids such as glyceryl monolaurate; tetraglycol (tetrahydrofurfuryl alcohol polyethylene glycol ether); tetraethylene glycol (ethanol,2,2'-(oxybis(ethylenoxy))diglycol); $C_6$-$C_{20}$ alkyl pyrrolidone carboxylates; polyethylene glycol; propylene glycol; 2-(2-ethoxyethoxy)ethanol; diethylene glycol monomethyl ether; N,N-dimethyldodecylamine-N-oxide and combinations of the foregoing. Alkylaryl ethers of polyethylene oxide, polyethylene oxide monomethyl ethers, polyethylene oxide dimethyl ethers, glycerol, and N-methyl pyrrolidone are also suitable. The terpenes are another useful class of pharmaceutical excipients, including pinene, d-limonene, carene, terpineol, terpinen-4-ol, carveol, carvone, pulegone, piperitone, menthone, menthol, neomenthol, thymol, camphor, borneol, citral, ionone, and cineole, alone or in any combination. Examples of other additives include tackifiers, plasticizers, and anti-oxidants.

Exemplary pharmaceutically active agents (also referred to as "drugs") that can be included in the reservoir are capable of local or systemic effect when administered to the skin. Some examples include clonidine, estradiol, nicotine, nitroglycerine, scopolamine, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone, testosterone, estradiol); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, and acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, buprenorphine); peptide hormones (e.g., human or animal growth hormones, LHRH); cardioactive products such as atriopeptides; proteinaceous products (e.g., insulin); enzymes (e.g., antiplaque enzymes, lysozyme, dextranase); antinauseants; anti-convulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatripan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect. Generally, the device will be in the form of a patch with a size suitable to deliver a selected amount of drug through the skin.

Generally, the device will have a surface area greater than about 1 $cm^2$, and sometimes greater than about 5 $cm^2$. Generally, the device will have a surface area of less than about 100 $cm^2$, and sometimes less than about 40 $cm^2$. In one embodiment, devices may be packaged individually in a foil-lined pouch for storage. In one embodiment, devices may alternatively be provided in a rolled or stacked form suitable for use with a dispensing apparatus.

In one embodiment the release liner is the same shape and size as the area of the adhesive portion of the device. It may be desirable to have one or more cuts or splits in the release liner to assist in removal of the adhesive portion from the liner.

In one embodiment the release liner has a larger area than the adhesive portion of the device, thereby providing an extended liner. The distance that the release liner extends beyond the margins of the adhesive portion of the device can be any suitable distance, and may depend upon a number of factors including, for example, the size of the adhesive portion of the patch, the types of adhesive, backing, and liner employed, and the patient population using the patch. In one embodiment, the area of the release liner may be less than or equal to about 10 times, sometimes less than or equal to about 2.5 times, and often less than or equal to 1.5 times the area of the adhesive portion of the device. The distance that the liner extends may be uniform around the circumference of the patch or it may vary, for example, by providing a smaller circular patch on a square-shaped extended liner.

EXAMPLE

Transdermal patches having an extended liner were prepared as follows. A fentanyl-containing adhesive laminate on a release liner was prepared according to the general procedure of Example 12 of U.S. Patent Application Publication No. 2002/0119187 A1 (Cantor et al.). The drug-in-adhesive layer was coated at a width of approximately 2.25 inch (5.72 cm) onto a first silicone release coated polyester web that was 5.0 mil (127 µm) thick, oven dried to a thickness of approximately 2.5 mil (63.5 µm), laminated to a 2.0 mil (51 µm) thick laminate film of polyethylene terephthalate (PET)/ethylene vinyl acetate (Scotchpak™ 9732, 3M Company, St. Paul, Minn.) to prepare an adhesive laminate on the silicone coated web, and wound into rollstock.

The adhesive laminate on the silicone coated web was converted according to the general process shown in FIGS. 2, 10, 11, and 12. The adhesive laminate was die cut into two product ribbons of patch shaped sections having tie points connecting adjacent patches in each ribbon. The remaining three strands of material (one central strand and the two edges of the rollstock) were wound on spools using a differential winder and discarded. The patch-shaped sections of each ribbon had a width 954 of 0.806 inch (2.05 cm), length 952 of 1.125 inch (2.86 cm), and radius 956 of 0.250 inches (0.635 cm). Each adjacent patch shaped section was connected by two tie points with tie-point spacings 958, 960 of 0.280 inch (0.711 cm) and 0.526 inch (1.34 cm), respectively. Each tie point was approximately 16 mil (406 µm) wide. The lane spacing 962 between the two ribbons was 0.124 inches (0.315 cm).

The two ribbons were spaced apart from each other in the cross-web (or transverse) direction to a center-to-center distance of 1.356 inches (3.444 cm) using a ribbon guide to prepare for subsequent placement onto a second web. The ribbons were pulled over a nosebar 155, as shown in FIG. 2 and the patch shaped sections of adhesive laminate were transferred to a second silicone coated polyester web that was 5 mil (127 µm) thick supported by a support roll 160. The closest spacing between the nose bar and support roll was approximately 40 mil (1020 µm) and the take-off angle was approximately 37 degrees. The length of adhesive laminate overhanging the nosebar while the patches were being spaced in the longitudinal direction was approximately 0.2 inches (0.5 cm). The second web was advanced at a continuous speed and the first web was moved in an intermittent motion. The intermittent motion of the first web was programmed to place the patches with a downweb, center-to-center spacing of 1.625 inches (4.128 cm). The transferred patches were then fully laminated to the second web by an ironing roll 170, followed by a nip, comprised of a rubber roll and a metal roll, which also pulled and controlled the continuous motion of the second web.

The second web was then cut to produce a rectangular liner shape having a length of 1.500 inch (3.810 cm) and a width of 1.106 inch (2.809 cm) with 0.400 inch (1.016 cm) corner radii. The liner was larger than the transferred patch, thus preparing a transdermal drug delivery device with an extended liner. The transferred adhesive laminate patches were aligned with previously placed die cuts in the second liner, so that each final device had a liner-split extending across the entire liner to facilitate removal of the patch. The converting process had an approximately 87% yield of the input adhesive laminate being converted into finished devices, excluding the two discarded edges.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

The invention claimed is:

1. A method of handling an adhesive laminate comprising:
providing an adhesive laminate releasably adhered to a first web; wherein the adhesive laminate comprises a plurality of cut or punched sections and wherein adjacent sections of the adhesive laminate remain joined to one another in the longitudinal direction of the web through one or more tie points;
providing a first supporting structure;
leading the first web over the first supporting structure;
providing a second supporting structure adjacent to the first supporting structure;
providing a second web having a release surface;
leading the second web over the second supporting structure, wherein the second web is oriented such that the release surface of the second web faces the first supporting structure;
attaching a leading portion of a first section of adhesive laminate from the first web to the release surface of the second web; and
advancing the second web such that the first section of the adhesive laminate is detached from a second section of adhesive laminate and the leading edge of the second section of adhesive laminate is adhered to the second web in a spaced apart configuration from the trailing edge of the first section of the adhesive laminate.

2. A method according to claim 1 wherein the first supporting structure is a nose bar.

3. A method according to claim 1 wherein the first supporting structure is a support roll.

4. A method according to claim 1 wherein the second supporting structure is a nose bar.

5. A method according to claim 1 wherein the second supporting structure is a support roll.

6. A method according to claim 1 wherein the gap between the first supporting structure and the second supporting structure is less than or equal to the length of a single cut or punched section of the adhesive laminate.

7. A method according to claim 1 wherein the advancing step is repeated thereby providing a plurality of spaced apart sections of adhesive laminate adhered to the second web.

8. A method of handling an adhesive laminate comprising:
providing an adhesive laminate releasably adhered to a first web; wherein the adhesive laminate comprises a plurality of cut or punched sections and wherein adjacent sections of the adhesive laminate remain joined to one another in the longitudinal direction of the web through one or more tie points;
transferring a first section of adhesive laminate and a portion of an adjacent second section of adhesive laminate to a second web;
accelerating the second web relative to the first web, thereby detaching the first section from the second section.

9. A method according to claim 8 wherein the accelerating step is repeated, thereby providing a spaced apart sections of adhesive laminate adhered to the second web.

10. A method according to claim 8 wherein the adhesive laminate comprises a drug.

11. A method according to claim 8 wherein one of the first web or the second web is moved in a continuous motion.

12. A method according to claim 8 wherein one or both of the first web and the second web is moved in an intermittent motion.

13. A method according to claim 8 wherein the second web is advanced at a faster speed than the first web during the step of detaching the first section of the adhesive laminate from the second section of adhesive laminate.

14. A method according to claim 8 wherein the first and second web are moved at a substantially the same speed prior to the step of accelerating the second web relative to the first web.

15. A method according to claim 8 wherein the speed of the first web is decreased in order to accelerate the second web relative to the first web.

16. A method according to claim 8 wherein the cut or punched sections of adhesive laminate have the shape of an adhesive patch.

17. A method according to claim 8 wherein the first web is substantially fully adhered to the second web prior to the step of detachment from the second section of adhesive laminate.

18. A method according to claim 8 further comprising the step of cutting or punching the second web around a section of adhesive laminate, thereby providing an adhesive patch having an extended liner.

19. A method according to claim 8 wherein drug-containing waste between the cut or punched patch-shaped sections of adhesive laminate remains on the first web as the patch-shaped sections of adhesive laminate are transferred to the second web.

20. A method according to claim 8 wherein the tie points have a thickness of less than about 1.0 mm.

* * * * *